(12) United States Patent
Pham et al.

(10) Patent No.: US 10,136,957 B2
(45) Date of Patent: Nov. 27, 2018

(54) LEAK RESISTANT ARTICLE

(71) Applicant: Ansell Limited, Richmond, Victoria (AU)

(72) Inventors: Thi Hao Pham, Selangor D.E. (MY); Huay Ling Low, Melaka (MY)

(73) Assignee: Ansell Limited, Victoria (AU)

( * ) Notice: Subject to any disclaimer, the term of this patent is extended or adjusted under 35 U.S.C. 154(b) by 129 days.

(21) Appl. No.: 15/336,007

(22) Filed: Oct. 27, 2016

(65) Prior Publication Data

US 2017/0119485 A1 May 4, 2017

Related U.S. Application Data

(60) Provisional application No. 62/248,438, filed on Oct. 30, 2015.

(51) Int. Cl.
*A61B 42/30* (2016.01)
*A61B 42/10* (2016.01)
*A41D 19/00* (2006.01)
*C08J 7/04* (2006.01)

(52) U.S. Cl.
CPC ............ *A61B 42/30* (2016.02); *A41D 19/001* (2013.01); *A41D 19/0082* (2013.01); *A61B 42/10* (2016.02); *C08J 7/045* (2013.01); *C08J 2300/26* (2013.01); *C08J 2347/00* (2013.01); *C08J 2400/12* (2013.01)

(58) Field of Classification Search
CPC .. A41D 19/001; A41D 19/0082; A61B 42/10; A61B 42/30; C08J 2347/00; C08J 2400/12; C08J 7/045; C08J 2300/26
See application file for complete search history.

(56) References Cited

U.S. PATENT DOCUMENTS

| | | | |
|---|---|---|---|
| 2,642,416 A | 6/1953 | Ahlbrecht et al. |
| 2,803,615 A | 8/1957 | Ahlbrecht et al. |
| 2,826,564 A | 3/1958 | Bovey et al. |
| 2,839,513 A | 6/1958 | Ahlbrecht et al. |
| 2,841,573 A | 7/1958 | Ahlbrecht et al. |
| 3,256,230 A | 6/1966 | Johnson, Jr. et al. |
| 3,462,296 A | 8/1969 | Raynolds et al. |
| 3,484,281 A | 12/1969 | Guenthner et al. |
| 3,594,353 A | 7/1971 | Domba |
| 3,636,085 A | 1/1972 | Kleiner |
| 5,224,221 A | 7/1993 | Richardson et al. |
| 5,524,294 A | 6/1996 | Richardson et al. |
| 6,709,725 B1 | 3/2004 | Lai et al. |
| 7,056,845 B2 | 6/2006 | Waeber et al. |
| 8,530,016 B2 | 9/2013 | Wang et al. |
| 2010/0112204 A1 | 5/2010 | Marte et al. |
| 2010/0159195 A1 | 6/2010 | Quincy, III et al. |
| 2011/0287553 A1 | 11/2011 | Hassan et al. |
| 2012/0090074 A1 | 4/2012 | Venables et al. |
| 2014/0165263 A1 | 6/2014 | Pham et al. |
| 2016/0033418 A1 | 2/2016 | Eng et al. |

FOREIGN PATENT DOCUMENTS

| | | |
|---|---|---|
| CA | 697656 A | 11/1964 |
| CA | 942900 A | 2/1974 |
| DE | 1419505 A1 | 1/1969 |
| FR | 1562070 A | 4/1969 |
| FR | 1568181 A | 5/1969 |
| GB | 971732 | 10/1964 |
| WO | WO-2016011480 A1 | 1/2016 |

OTHER PUBLICATIONS

"Hydrophobic silica", Wikipedia.
Jin et al., "Super-Hydrophobic PDMS Surface with Ultra-Low Adhesive Force", Macromolecular Rapid Communications, vol. 26, Issue 22, pp. 1805-1809, Nov. 14, 2005.
Caillot et al., "Anticipated Detection of Imminent Surgeon-Patient Barrier Breaches. A Prospective Randomized Controlled Trial Using an Indicator Underglove System", World Journal of Surgery, vol. 30, Issue 1, pp. 134-138, Jan. 2006.
Roach et al., "Progess in Superhydrophobic Surface Development", Soft Matter, vol. 4, Issue 2, pp. 224-240, Jan. 2008.
Qingwei et al., "Fabrication of a Highly Robust Polymer Superhydrophobic Surfaces by Replica-Molding Method", pp. 4, Mar. 13, 2013.
Latthe et al., "Superhydrophobic Surfaces Developed by Mimicking Hierarchical Surface Morphology of Lotus Leaf", Molecules, vol. 19, Issue 4, pp. 4256-4283, Apr. 4, 2014.
Wang et al., "Multifunctional Superhydrophobic Surfaces Templated From Innately Microstructured Hydrogel Matrix", Nano Letters, vol. 14, Issue 8, pp. 4803-4809, 2014.

*Primary Examiner* — Arti Singh-Pandey
(74) *Attorney, Agent, or Firm* — Moser Taboada

(57) ABSTRACT

Provided, among other things is a leak-resistant elastomeric barrier comprising: an elastomeric barrier comprising elastomeric polymer, having two sides, and coated on at least a portion of a first side with a highly hydrophobic coating such that the initial contact angle with water is about 130° or more, and that contact angle does not decay by more than about 10% over 40 minutes. In embodiments the highly hydrophobic coating comprises hydrophobic silica particles are disposed on a hydrophobic coating disposed on the first side, for example with a hydrophobic coating comprises that a fluorocarbon compound, a polypropylene wax, a polyethylene wax, or a mixture thereof.

23 Claims, 6 Drawing Sheets

LEAK RESISTANT ARTICLE

CROSS-REFERENCE TO RELATED APPLICATIONS

This application claims the benefit of priority to U.S. Application No. 62/248,438, filed Oct. 30, 2015, and is incorporated herein by reference in its entirety.

Embodiments of the present invention generally relate to elastomeric articles such as gloves that resist the leakage of aqueous fluids through small holes; and to combination gloves for detecting fluid leakage through an outer or inner glove of the combination.

In detecting the leakage of aqueous fluids, such as blood, it is known to utilize double gloves of elastomer materials with space allowing fluid to flow in between the layers. The elastomers of the layers typically have contrasting color so that a fluid collected between the two layers changes the visual impact. See, U.S. Pat. No. 5,224,221 and U.S. Pat. No. 5,524,294. Nonetheless, in the surgical setting, the visual obstruction caused by blood, and the low visual impact of the contrasts obtained have meant the breaches are not infrequently un-noticed by medical users. Caillot et al., World J Surg. 2006 January; 30(1):134-8. Venables, US Patent Application 2012/0090074, describes a double glove system which seeks to enhance the contrast obtained upon breach, but nonetheless comes up short. U.S. Pub. No. 2016-0033418, filed 22 Jul. 2015 describes important improvements to breach detection.

As part of the leak detection system outlined above, it can be important to reduce the adhesion of blood to elastomer, so that the blood does not interfere in detecting color or contrast changes generated by fluid resident between the two glove layers. It has now been discovered that adhesion reduction can be improved to the point that 3 mm cut linear holes resist leaking aqueous fluid into which the gloves are immersed.

As such, with this improvement the combination gloves of U.S. Pub. No. 2016-0033418 are improved in that they both effectively signal leakage, and they further resist leakage in for example a surgical environment. Moreover, the leak-resistant feature can be used in any other context where an elastomeric article is used to insulate an object from a possible aqueous contaminant.

SUMMARY

Provided, among other things is a leak-resistant elastomeric barrier comprising: an elastomeric barrier comprising elastomeric polymer, having two sides, and coated on at least a portion of a first side with a hydrophobic coating (e.g., hydrophobic silica particles) such that the initial contact angle with water is about 130° or more, and that contact angle does not decay by more than about 10% over 40 minutes. In embodiments the hydrophobic silica particles are disposed on a hydrophobic coating disposed on the first side, for example with a hydrophobic coating comprises that a fluorocarbon compound, a polypropylene wax, a polyethylene wax, or a mixture thereof.

Further provided is a barrier glove wherein the barrier is formed to provide the hand protective part of the barrier glove. In embodiments, the barrier glove is a top, outer glove of a combination glove comprising a bottom, inner glove. In embodiments, the combination glove is for detecting breaches of hydrophilic or aqueous fluid wherein: (a) the top glove has an inner surface, namely the inner-barrier surface, the elastomer barrier of the top glove being translucent or transparent; (b) the bottom glove has an outer surface, namely the outer-backstop surface, the bottom glove comprising an elastomer layer that is darker than the top elastomer layer; and (c) there is a space or seam between the gloves in which the hydrophilic or aqueous fluid can flow, wherein to either the inner-barrier or the outer-backstop surface has been applied a hydrophilicity promoting composition, wherein the hydrophilicity promoting composition enhances the spreading in the space or seam of any of the hydrophilic or aqueous fluid that breaches the top elastomer or bottom layer.

In embodiments, the leak-resistant barriers further resist the resists the permeation of bacteria through a 3 mm linear cut hole.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

Figure 1A:
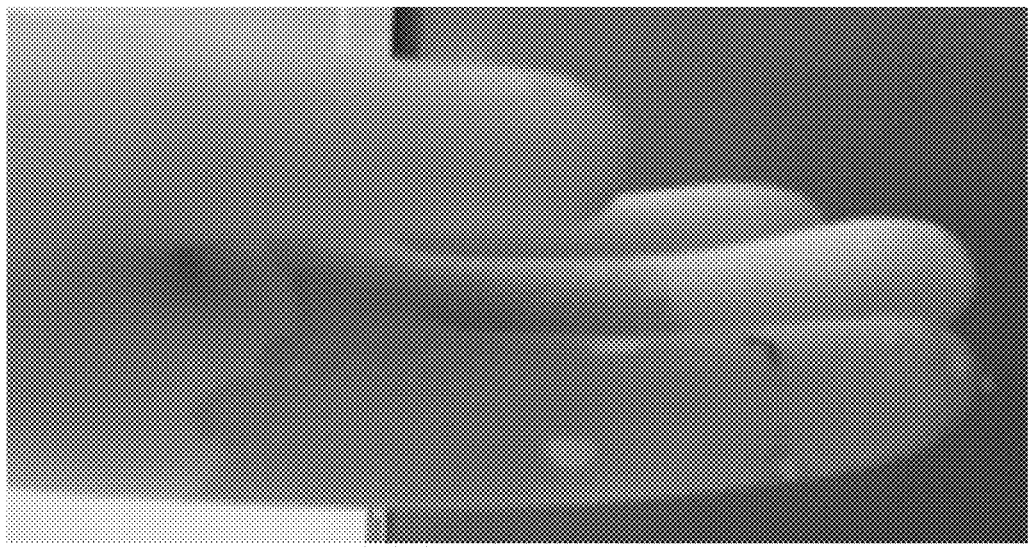
FIG. 1A shows a control outer glove (Ansell Textured Polyisoprene) in combination with the inner glove prior to dipping.
Figure 1B:
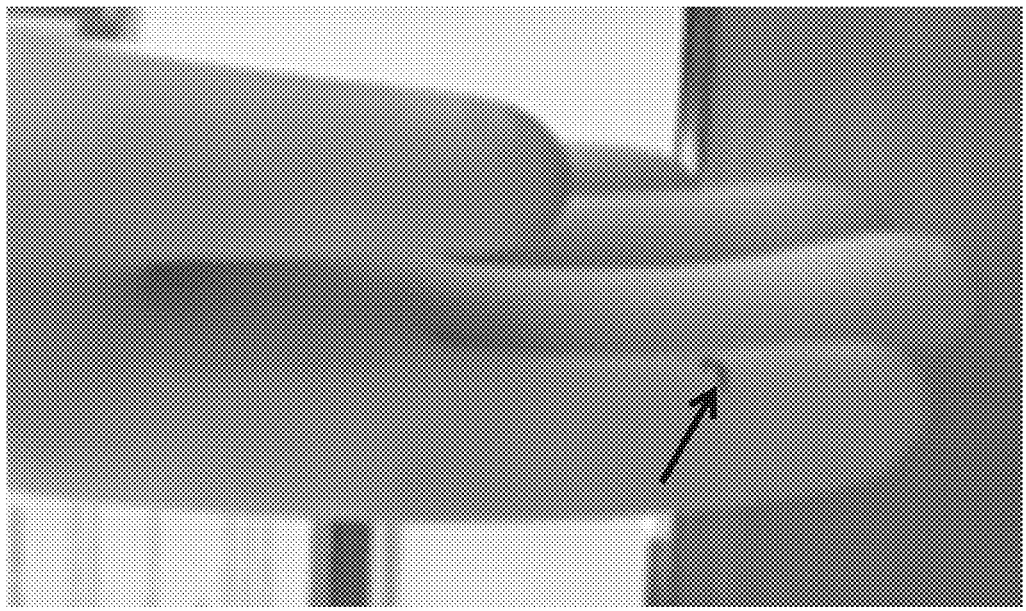
FIG. 1B shows the glove combination after 1 minute of dipping in water.

While the invention is described herein by way of example using several embodiments and illustrative drawings, those skilled in the art will recognize that the invention is not limited to the embodiments of drawing or drawings described. It should be understood that the drawings and detailed description thereto are not intended to limit the invention to the particular form disclosed, but on the contrary, the invention is to cover all modification, equivalents and alternatives falling within the spirit and scope of the present invention as defined by the appended claims.

The headings used herein are for organizational purposes only and are not meant to be used to limit the scope of the description or the claims. Also, as used throughout this application, the word "may" is used in a permissive sense (i.e., meaning having the potential to), rather than the mandatory sense (i.e., meaning must). Similarly, the words "include," "including," and "includes" mean including, but not limited to. The word "glove" means glove or glove liner.

DETAILED DESCRIPTION

A. Leak Resistance

As outlined in for example U.S. Pub. No. 2014-0165263, an outer surface of an outer glove can be treated to repeal aqueous fluid. Previously, the best repellency was found with a HeiQ® Barrier RCF fluorocarbon coating and a microparticle coating, such as HeiQ® Barrier HM. There, with for example polyisoprene material, the highest contact angle obtained was about 140°, and this contact angle notably decayed to about 110° within 60 minutes. In contrast, Applicant has now found that polyisoprene can be coated with highly hydrophobic material that provides an initial contact angle of about 140° or higher, with no decay in the contact angle beyond about 10% or less over the next 40 or 60 min. In embodiments, the decay is about 6% or less over the next 40 min. In embodiments, the initial contact angle is about 145° or higher, with the decay as outlined above.

It is anticipated that the initial contact angle will vary with different elastomers. It is also anticipated that the contact angle will be stable. In embodiments, the initial contact angle is 130° or higher (such as 135° or higher, or 140° or higher, or 145° or higher). In embodiments, the decay in the contact angle is about 10° or less over the next 40 or 60 min. In embodiments, decay in the contact angle is about 6° or less over the next 40 or 60 min. In embodiments, decay in the contact angle is about 5° or less over the next 40 or 60 min.

When the treated elastomer is formed into a glove and used as the outer glove of a double glove combination, it has now been found that the treated glove with a 3 mm linear hole (nearly ⅛ inch) can be dipped in dyed water or expired blood for 1 or 5 minutes, and nonetheless there is no indication of leakage into the space between the two gloves. Thus, the user of such gloves has protection against the small holes that may arise during use of the gloves, such as from snags or needle pricks.

To achieve this level of water repellency, the elastomer surface can be for example first treated with a substance that increases hydrophobicity, such as a fluorocarbon compound (e.g., fluoropolymer) or wax, such as a polyethylene or polypropylene wax, or another hydrophobic wax, providing a hydrophobic coating. Such compounds are described further below. A hydrophobic coating can comprise a mixture of substances that increase hydrophobicity, such as fluorocarbon compound and wax (e.g., polyethylene or polypropylene wax).

Alternatively, or thereafter, for example, hydrophobic particles (e.g., hydrophobic silica particles) can be applied. Hydrophobic silica has chemically bonded hydrophobic groups. The hydrophobic groups can be for example alkyl groups or polydimethylsiloxane chains. Without being bound by theory, it is believed that spray application, for example with a hydrocarbon aerosol agent, aids in self-assembly of the hydrophobic silica particles. The presence of a strong, water miscible solvent that evaporates readily is also believed to be helpful. Strong solvents can be for example solvents with a Polarity Index from about 4 to about 6, or a dielectric constant (20° C.) of about 5 to about 40. (The Polarity Index is a proprietary, but well recognized in the chemical arts, rating system that provides a relative measure of the degree of interaction of the solvent with various polar test solutes.) Exemplary strong solvents of this type include for example acetone, ethyl acetate or methyl acetate.

Hydrophobic particles are believed (without being bound by theory) to create a certain amount of porosity within the nanostructure, which may reduce the area truly in contact with the liquids, accentuating the hydrophobicity.

The elastomer surface with water contact angle of about 140° or more is believed to be able to repel liquids completely because any liquid placed on the surface rolls off without touching the underlying surface. In addition, the inventors have found that the coating not only repels liquids but also prevents them from approaching and ingressing a small cut hole in a glove that has the surface; even after immersing this glove in the liquids for 5 minutes.

In embodiments, the hydrophobic coating is also applied as a spray, such as an aerosol-driven spray. The aerosol agent can be hydrocarbon. The application spray can include volatile solvents that dissolve or swell or otherwise provide for even application of the hydrophobic coating.

In embodiments, the hydrophobic coating is Rust-Oleum NeverWet base coat material (believed to contain fluoropolymer and wax). In embodiments, the hydrophobic silica particles are provided with Rust-Oleum NeverWet top coat material. Both available from Rust-Oleum Corp., Vernon Hills, Ill. Other coatings that can be used and are available on the market, which comprise a base coat containing Fluoropolymer and wax and top coat containing hydrophobic silica particles, include for example Ultra-ever Dry (UltraTech International, Inc., Jacksonville, Fla.), and Fluorothane AD (Cytonix Corporation, Beltsville, Md.).

In embodiments, the hydrophobic coating is applied in a fluid that is substantially free of water. For example, the water content of the solvent component is about 2% or less by weight, or about 1% or less, or about 0.5% or less, or about 0.2% or less, or about 0.05% or less. In embodiments the hydrophobic silica particles are applied in a fluid that is substantially free of water.

The fluid repellency of elastomeric barriers provided by the invention can be applied for example to natural rubber (NR), polychloroprene (CR), acrylonitrile butadiene copolymer (NBR) (such as carboxylated acrylonitrile butadiene copolymer), polyisoprene (PI), polyurethane (PU), styrene-butadiene, butyl rubber (copolymer of isobutylene with isoprene, or polymer of isobutylene), or combinations thereof. PI and NBR gloves are of particular interest.

Where a tie layer of elastomer and hydrophobic component is used, the layer can be formed from a latex containing from about 5 to about 50 parts per hundred (PHR) rubber (rubber dry weight) of the dry weight of the hydrophobic components.

The fluid repellency property includes the property of repelling blood. Thus, the invention is very useful for surgical gloves, reducing the burden to the surgical worker of carrying substantial blood from one surface to another. If the gloves are a combination for detecting aqueous leaks, then reduced blood adherence also increases the visual impact of the detection system.

In embodiments, the elastomeric barriers are formed by a dipping process. In embodiments, the dipping process utilizes a coagulant.

When during use a outer article leak is detected, inner (if present) and outer articles can be replaced.

Articles according to the invention can include any protective wear incorporating the elastomeric barrier as an outer layer. For example, boots or booties, gloves, protective suits, protective facial wear, condoms, and the like.

Process of Forming Water Repellant Surface (Leak Resistant Surface)

The process of forming the leak resistant surface can include:

TABLE A

Optionally applying a hydrophobic coating solution (comprising non-particulate hydrophobic component(s)), suspension or dispersion to an elastomer surface.
Optionally, the application is by aerosol spraying. Optionally, two aerosol sprayed coats are applied. The hydrophobic coating solution can be substantially free of elastomer, meaning that there is not enough elastomer to form a structural layer.
Optionally applying a "tie layer" by blending the hydrophobic component with synthetic or natural rubber latex (or combination, as described elsewhere herein) and optionally applying this prior to applying the hydrophobic coating solution. In embodiments, the tie layer is used in place of the hydrophobic coating solution application recited above, and provides a hydrophobic coating.
Optionally using imprinting method to create microstructure or nanostructure on the elastomer surface prior to applying the hydrophobic coating solution, thereby further limiting the contact surface with aqueous fluids.
Optionally drying the elastomer surface.
Applying a hydrophobic particle suspension to the elastomer surface.
Optionally, the application is by aerosol spraying. Optionally, two coats of aerosol spraying.
Drying the elastomer surface.

The process of forming the leak resistant surface can include the following optional steps or optionally more detailed steps:

TABLE B

Ensure the elastomer surface is dry and free of residue chemicals.
Base Coat Process A aerosol can of base coat material (typically, hydrophobic coating solution, e.g., Rust-Oleum NeverWet base coat) is shaken vigorously, continuing for one minute after mixing ball begins to rattle. The can should be shaken regularly during usage. A test spray can be done on a cardboard to obtain spray pattern feel.
Shaking should be continued while spraying.
Base coat material is sprayed approximately 6-12 inches from the elastomer surface.
Two light coats are sprayed (e.g., for one: right to left; for the other: up and down).
After spraying this first coating of base coat, it is left to dry for e.g. 30 minutes.
Optionally, A second coat can be sprayed if desired, also waiting for 30 minutes drying time before moving to the next step.
Top Coat Process An aerosol can of the top coat material (typically, hydrophobic particle suspension, e.g., Rust-Oleum NeverWet top coat) is shaken vigorously, continuing for one minute after the mixing ball begins to rattle. It should be shaken regularly during usage. Test spray can be done on a cardboard to obtain spray pattern feel.
Shaking should be continued while spraying.
The top coat material should be sprayed over the base coat approximately 6-12 inches from the elastomer surface.
Two light coats are sprayed (e.g., for one: right to left; for the other: up and down). Care is taken no to soak the surface.
After about 2 minutes drying time, additional coatings of up to two light coatings can be applied.
The coatings are left at room temperature to cure overnight.

B. Leak Detection Combination

The combination glove of the invention has two glove components, an outward or top glove, and an inward or bottom glove. It will be understood that the combination can be worn with other gloves, generally gloves worn inward of the bottom glove.

Provided, among other things, is a combination glove for detecting breaches of hydrophilic or aqueous fluid comprising: (a) an top, "barrier" elastomer layer with an inner surface, namely the inner-barrier surface, the top elastomer layer being translucent or transparent; (b) an bottom, "backstop" elastomer layer with an outer surface, namely the outer-backstop surface, the bottom elastomer layer being darker than the top elastomer layer; and (c) a space or seam between the layers in which the hydrophilic or aqueous fluid can flow, wherein to either the inner-barrier or the outer-backstop surface has been applied a hydrophilicity promoting composition of (i) a polyvinyl alcohol or (ii) an alkyl-aryl compound or a siloxane compound with the foregoing having pendent one to two oxy-polymers, (iii) a quaternary amine including an alkyl of C8 to C24, or (iv) a mixture of the foregoing, wherein the oxy-polymer is (1) a polyoxyalkylene polymer that is predominantly oxyethylene or (2) a polyvinyl alcohol, wherein the hydrophilicity promoting composition enhances the spreading in the space or seam of any of the hydrophilic or aqueous fluid that breaches the top or bottom elastomer layer. In embodiments, the hydrophilicity promoting composition further comprises a hydrophilic compound of carbon, hydrogen and oxygen wherein the carbon number is 2 to 8, such as a polyol. It will be understood that not all of the compound quantities in a hydrophilicity promoting composition applied to an elastomer surface will necessarily become associated with the surface, and that the volatile compounds will substantially be removed in the application process.

Figure 6A:
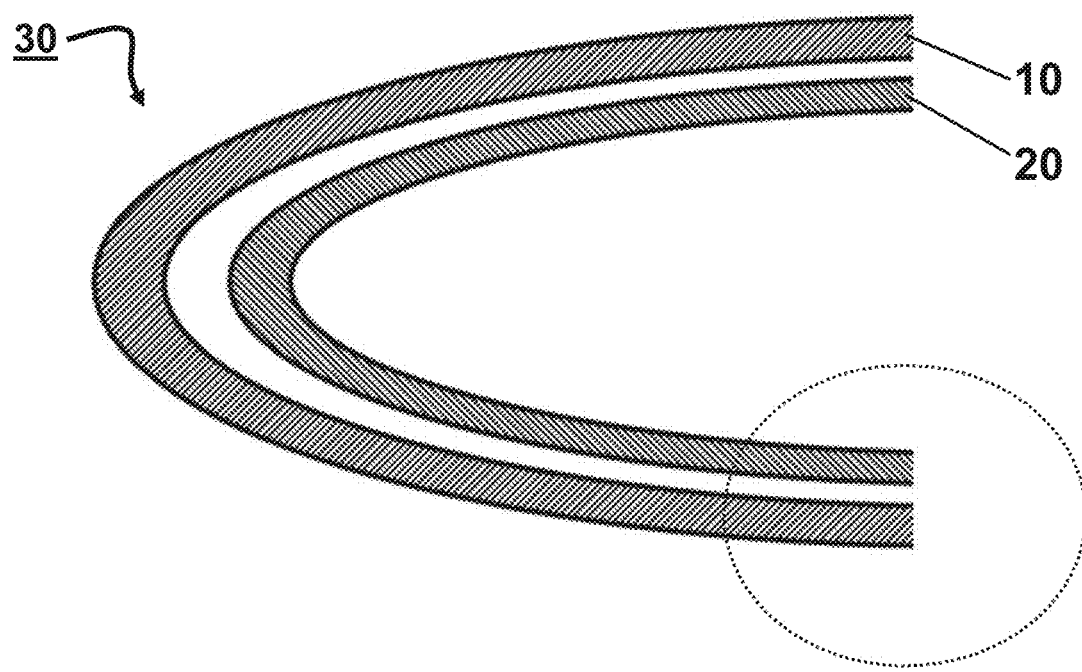
FIG. 6A shows the tip of a finger 30 of a combination glove.
Figure 6B:
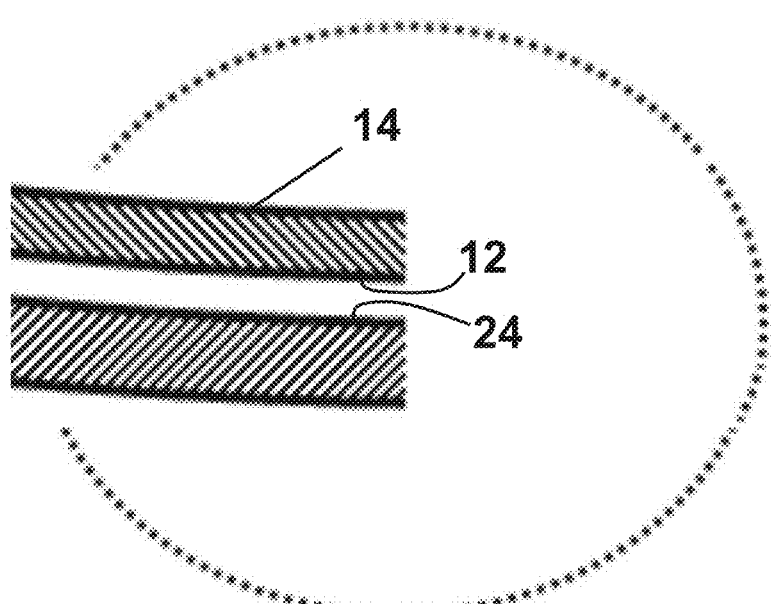
FIG. 6B shows a portion of FIG. 6A.

Illustrated in FIG. 6A is the tip of a finger 30 of a combination glove. Barrier layer 10 has an outer surface 14 and an inner surface 12 (inner-barrier surface), as shown in FIG. 6B. Backstop layer 20 has an outer surface 24 (outer-backstop surface). Outer surface 14 can be coated to make that surface leak-resistant. If for example, inner-barrier surface 12 is treated to be hydrophobic so as to satisfy the claims, it is still leak resistant, though oriented opposite the most common source of leaks (which is outside of outer surface 14).

Further provided is a method of conducting surgery comprising: (a) a surgical worker donning a said combination glove; and (b) conducting a medical procedure in which the combination glove is exposed to biological fluids from a patient. The method can further comprise (c) the surgical worker removing the combination glove and replacing it with a second combination glove when the first combination glove darkens consistent with there being aqueous fluid between the top and bottom elastomer layers.

First Inner-Barrier or Outer-Backstop Surface

As described above, one of the inner-barrier or the outer-backstop surfaces in the combination is treated to render it hydrophilic (e.g., having affinity for water). In embodiments, it is the outer-backstop surface, i.e., the outer surface of the inner glove.

The polyvinyl alcohol is substantially hydrolyzed to reveal 80% or more (such as 90% or more, or 95% or more, or 98% or more) of the hydroxyl groups. The degree of polymerization can be from about 100 to about 3000. For example, the polyvinyl alcohol can be Exceval RS2117 (degree of polymerization 1,700, 99% hydrolysed) or Exceval HR3010 (degree of polymerization 1,000, 98% hydrolysed). Exceval polymers from Kuraray America Inc., Houston, Tex. In embodiments, the polyvinyl alcohol is used in conjunction with the hydrophilic compound such as polyol described below. In embodiments, the polyvinyl alcohol has an ethylene repeat along the main polymer chain.

In embodiments, for an alkyl-aryl compound having a pendent, from aryl, one to two oxy-polymers, the alkyl groups on the aryl are 1 to 2 in number, such as 1. In embodiments, one or more such alkyl is on average C16 or C17 or higher, such as C16 to about C32. In embodiments, one or more such alkyl is on average C8 or C10 or higher. In embodiments, the alkyl-aryl compound is used in conjunction with the hydrophilic compound such as polyol described below.

In embodiments, for siloxane compound having pendent one to two oxy-polymers, the compound is soluble in water. In embodiments, the siloxane is has 2 to 8 Si. In embodiments, the siloxane is oxides not linked to oxy-polymer are modified with C1 to C3 alkyl. In embodiments, the siloxane compound is used in conjunction with the hydrophilic compound such as polyol described below.

The oxy-polymer is present in 1 to 2 pendent groups, such as one. In embodiments, the oxy-polymer element(s) ((i) a poly-oxyalkylene polymer that is predominantly oxyethylene or (ii) a polyvinyl alcohol) on the alky-aryl compound has from about 8 to about 200 repeats, such as about 30 to about 100 repeats. The alkylene in poly-oxyalkylene polymer is ethylene or propylene. In embodiments, the poly-oxyalkylene polymer is polyoxyethylene. In embodiments, aryl is C6 or C10. In embodiments, aryl is C6. The linkage of aryl or siloxane to oxy-polymer is via an oxy bridge, or C1-C4 alkyl to oxy to the residue of oxy-polymer.

The quaternary amine has two to three alkyl substitutions of C1 to C2, and one to two alkyl of C8 to C24. In embodiments, the quaternary amine is used in conjunction with the hydrophilic compound such as polyol described below.

For example, one class of silicone compound modified with oxy-polymer is 2-[acetoxy(polyethyleneoxy)propypep-tamethyltrisiloxane (CAS No. 125997-17-3; AKA 3-(3-Hydroxypropyl)-heptamethyltrisiloxane, ethoxylated, acetate):

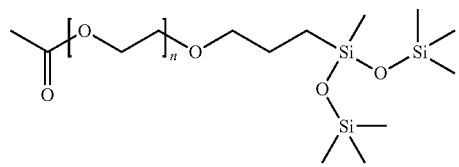

Another example is polyalkyleneoxide modified heptamethyltrisiloxane (CAS No. 27306-78-1):

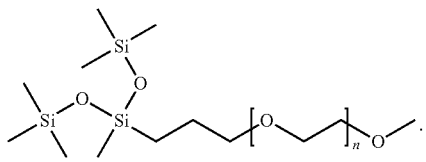

Another example is 3-(3-Hydroxypropyl)-heptamethyltrisiloxane, ethoxylated, Hydroxy-terminated (CAS No. 67674-67-3):

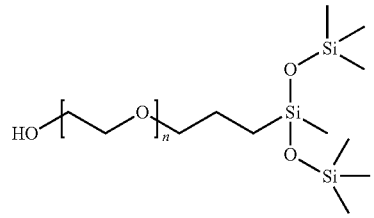

By a "hydrophilic" compound of carbon, hydrogen and oxygen wherein the carbon number is 2 to 8, it is meant that the compound (a) has a Log $P_{octanol/water}$ of −0.7 or lower (a 5:1 preference for water over octanol or higher) or (b) has a HLB (Hydrophilic-lipophilic balance) value>10. In embodiments, "hydrophilic is measured by LogP. In embodiments, "hydrophilic is measured by HLB. In embodiments, the hydrophilic compound is a di, tri or per-hydroxylated compound of C2 to C4, such as a polyol (such as glycerol, propylene glycol, 1,3-Butanediol, 1,2-Pentanediol, 1,2-hexanediol, or sorbitol) or sodium lactate.

Second Inner-Barrier or Outer-Backstop Surface

In embodiments, the other of the inner-barrier or the outer-backstop surfaces in the combination is treated to render it hydrophobic. For example, it can comprise a sublayer of film-forming polymer (such as polyurethane) and wax, such as described in U.S. Pat. No. 6,709,725, which is incorporated herein in its entirety for its teachings on making a hydrophobic surface. As discussed in the '725 patent, the treatment to render hydrophobic can include contacting the sublayer with a silicone/surfactant emulsion.

In embodiments, the inner surface of the outer glove is treated to render it hydrophobic, such as described in U.S. Pat. No. 6,709,725.

Outer Glove, Outer Surface

In embodiments, the outer surface of the outer glove of the combination glove of the invention has been treated to increase water-repellency. In embodiments, that treatments is with fluorocarbon compounds (which can include further functionalities as long as they do not on the whole negate the hydrophobic effect). In embodiments, the treatment is with hydrophobic particles in combination with fluorocarbon compounds, optionally in further combination with wax compounds, as described in U.S. 2014-0165263, filed 16 Dec. 2013. In embodiments, the treatment is with hydrophobic particles in combination with fluorocarbon compounds, optionally in further combination with wax compounds, in combination with an overlaying treatment with a silicone composition, such as described in U.S. Ser. No. 2014-0165263. U.S. Ser. No. 2014-0165263 is incorporated herein in its entirety for its teachings on these surface treatments.

The high contrast indicator provide by the combination glove is more useful in a surgical setting if the outer glove is relatively free of obscuring blood. Hence, the surface treatments described herein can enhance breach detection.

The combination of coatings according to embodiments of the invention forms a barrier coating that is differentiated from prior repellent coatings based on conventional fluorine chemistry. Barriers coatings in accordance with the invention comprise a fluid repellency treatment providing a rough, 3D surface structure on which hydrophobic particles, for example, silica (silicon dioxide) micro-particles, are deposited onto a flexible substrate, thereby creating a super fluid repellent effect.

Embodiments according to the invention comprise a highly effective combination for increasing the fluid repellency of elastomeric barriers, which may be used with elastomeric polymers of the type used for forming flexible surgical gloves, such as without limitation natural rubber (NR), polychloroprene (CR), acrylonitrile butadiene copolymer (NBR) (such as carboxylated acrylonitrile butadiene copolymer), polyisoprene (PI), polyurethane (PU), styrene-butadiene, butyl rubber (copolymer of isobutylene with isoprene, or polymer of isobutylene), or combinations thereof.

Silicone coatings that can be used with embodiments according to the invention include a formulation comprising a dimethicone emulsion, or a formulation comprising a cationic emulsion of an amine-functional silicone polymer, or a combination thereof, or one of the foregoing in combination with wax emulsion. The was can be, for example, a synthetic wax, such a polyethylene or polypropylene wax. The wax can be non-ionic. Such a silicone coating can be, for example, applied over the top coat described above.

Microparticle dispersions that can be used with embodiments according to the invention include wherein the hydrophobic micro-particles can be those described in, for example, U.S. Publ. No. 2010/0112204, US Publ. No. 2010/0159195, or U.S. Pat. No. 7,056,845, the entire disclosures of which are herein incorporated by reference in their entireties. The micro-particles of U.S. Publ. No. 2010/0112204 are reacted with linking reagents, followed by reaction with hydrophobic groups that attach to the resultant linking groups. Hydrophobic entities include C3-C24 hydrocarbon or C2-C12 perfluorinated carbon backbones. The micro-particles may also comprise nanoparticles, so long as the ability to induce a lotus effect with water is retained. For example, the size range can be about 0.01 to about 10 micrometers. Other micro-particles include silica particles.

Hydrophobic chemicals for use with embodiments of the invention also include known commercial products, for example, Softgard M3 (soft chemicals, Italy), Oleophobol 7752 (Huntsman, Germany), Ruco-Gard AIR and Ruco-Dry DHY (Rudolf Chemie, Germany), Scotchgard® (3M Inc., Maplewood, Minn.), Zepel-B™ (Dupont, Wilmington, Del.), anionic perfluoropolyether based polyurethane and polytetrafluoroethylene (Fluorolink® 5049), and perfluoropolyether based triethosilane (Fluorolink® S10, available from Ausimont, Thorofare, N.J.), perfluoroalkyl acrylic copolymer (such as Zonyl® 8300 available from Ciba Specialty, High Point, N.C.; and Scotchban™ FC-845 available from 3M, St. Paul, Minn.), perfluoroalkyl urethane (such as L-8977 available from 3M, St. Paul, Minn.), perfluoropolyether-modified polyurethane dispersion (such as Fluorolink™ P56 available from Ausimont, Thorofare, N.J.), fluorinated silicone polyester (such as Lambent™ WAX available from Lambent Technologies, Fernandina Beach, Fla.), polychlorotrifluoroethylene (such as Aclon™ PCTFE available from Honeywell, Morristown, N.J.), polyvinylidene fluoride dispersion (such as Unidyne™ TG available from Daikin America, New York, N.Y.), tetrafluoroethylene-hexafluoropropylene co-polymer (such as Dyneon™ FEP available from 3M, Parsippany, N.J.), polyperfluoroethoxymethoxydifluoroethyl PEG phosphate (such as Fomblin™ HC/2-1000 available from Solvay Solexis, Houston, Tex.), Oleophobol® CP-SLA (an aqueous dispersion of perfluorinated acrylic copolymer), like hydrophobic chemicals, and combinations thereof.

A variety of fluorochemical, fluid repellent compounds suitable for use in accordance with embodiments of the present invention are known and are commercially available. One particular group of fluorochemical repellents are the polymers obtained by polymerizing an ethylenically unsaturated fluorochemical compound. The ethylenic unsaturation may be either in the alcohol or the acid portion of the ester molecule. Typically, the unsaturated radical in the alcohol portion of the ester may be the allyl radical or the vinyl radical. Typical unsaturated acids used to prepare the ester include acrylic acid, methacrylic acid and crotonic acid. In general, the perfluoro portion of the molecule is in the saturated portion of the molecule. The unsaturated portion of the molecule is typically not fluorinated in each instance. The acid and alcohols radicals may suitably contain from 2 to 6 carbon atoms excluding the carbonyl carbon of the acid. Examples of such monomers include vinyl perfluorobutyrate and perfluorobutyl acrylate. These monomers may be polymerized as homopolymers or as copolymers by normal emulsion polymerization techniques using free radical catalysts.

Examples of other suitable fluorochemical repellents for use in embodiments of the invention are those known and sold under the trademarks "Scotchgard® FC 208", "Scotchgard® FC 210", "Scotchgard® FC 232", and Scotchgard® FC 319", manufactured by the 3M Company, "Zepel™ B" manufactured by E. I. DuPont de Nemours and Co. and "Tinotop™ T-10" manufactured by Ciba-Geigy Ltd.

Of these materials "Scotchgard® FC 208" is an aqueous nonionic emulsion containing approximately 28% by weight of a modified fluorinated acrylic polymer: a substance believed to be of the following approximate general formula:

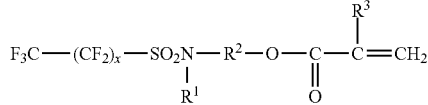

in which X is a value between 3 and 13 inclusive, $R_1$ is lower alkyl, such as methyl, ethyl, propyl, and the like, having 1-6 atoms $R_2$ is alkylene containing 1-12 carbon atoms and $R_3$ is H, methyl or ethyl. The product "Zepel™" is also available in emulsion form and while it is chemically different from the "Scotchgard®" products, it is a fluorochemical oil repellent containing fluorocarbon tails composed of $CF_2$ groups which may end in a terminal $CF_3$ group.

"Scotchgard® FC-319" is a solution of a compound similar to "FC-208" in an organic solvent. "Scotchgard® FC-232" is a dispersion of a fluorochemical resin in a mixture of water and methyl isobutyl ketone. "Zepel B™" is an aqueous cationic dispersion of a fluorochemical resin and is a product of E. I. Dupont de Nemours and Company. These products are believed to fall within the classes of compounds disclosed in the following patent specifications (compound descriptions incorporated herein by reference in their entirety): UK Pat. No. 971,732; Canadian Pat. No. 942,900; Canadian Pat. No. 697,656; French Pat. No. 1,568,181; French Pat. No. 1,562,070; German Pat. No. 1,419,505; U.S. Pat. No. 2,803,615; U.S. Pat. No. 2,826,564; U.S. Pat. No. 2,642,416; U.S. Pat. No. 2,839,513; U.S. Pat. No. 2,841,573; U.S. Pat. No. 3,484,281; U.S. Pat. No. 3,462,296; U.S. Pat. No. 3,636,085; U.S. Pat. No. 3,594,353; and U.S. Pat. No. 3,256,230.

Fluorolink® 5049 is a composition containing an anionic perfluoropolyether (PFPE) based polyurethane dispersion in water, polytetrafluoroethylene (PTFE) dispersion, isopropyl alcohol and methyl ethyl ketone, and is available from Solvay Solexis, Thorofare, N.J. Fluorolink® S10 is a composition containing a perfluoropolyether (PFPE)-based triethoxysilane dispersion in water, available from Solvay Solexis.

Wax dispersions for use as the hydrophobic chemical in accordance with embodiments of the invention, or as a supplement to a primary hydrophobic chemical (e.g., Freepel® 1225), include water-based wax dispersions such as, but are not limited to, synthetic wax (such as Freepel 11225 available from Noveon, Inc., Cleveland, Ohio); polyethylene wax (such as Michem™ ME available from Michelman, Cincinnati, Ohio; Luwax™ AF available from BASF, Parsippany, N.J.; Aquatec™ available from Eastman Chemical, Kingsport, Tenn.; and Jonwax™ available from S.C. Johnson Wax, Racine, Wis.); oxidized polyethylene wax (such as PoligenT WEI available from BASF, Parsippany, N.J.); ethylene acrylic acid copolymer EAA wax (such as Poligen™ WE available from BASF Parsippany, N.J.); ethylene vinylacetate copolymer wax (such as Aquacer™ available from BYK, Wallingford, Conn.); modified polypropylene wax (such as Aquaslip™ available from Lubrizol, Wickliffe, Ohio); silicone wax (such as DC 2503, DC2-1727, DC C-2-0563, DC 75SF and DC 580 available from Dow Corning, Midland, Mich.); Masilwax™ (available from Noveon, Cleveland, Ohio); Silcare™ 41M (available from Clariant, Charlotte, N.C.); fluoroethylene wax (such as Hydrocer™ available from Shamrock, Newark, N.J.); Carnauba wax (such as Slip-Ayd™ SL available from Daniel Products, Jersey City, N.J.); Fischer-Tropsch wax (such as Vestowax™ available from Degussa, Ridgefield, N.J.); and ester wax (such as Luwax™ E available from BASF, Parsippany, N.J.; and Lipowax™ available from Lipo, Paterson, N.J.), like waxes, and combinations thereof.

Optionally, fillers, resins, processing aids, cross-linkers, catalysts for cross-linking polymeric, elastomeric, or latex materials, such as natural rubber (NR), polychloroprene (CR), acrylonitrile butadiene copolymer (NBR) (such as carboxylated acrylonitrile butadiene copolymer), polyisoprene (PI), polyurethane (PU), styrene-butadiene, butyl rubber (copolymer of isobutylene with isoprene, or polymer of isobutylene), or combinations thereof and the like, as discussed above, can be used to further enhance the repellency and durability. These additional components can be incorporated within any elastomeric, polymeric, or latex compositions, which are then used with the hydrophobic chemical components of embodiments of the present invention to form a surface treated glove. Also, in certain embodiments, the elastomer for the unfoamed or foamed polymeric glove is predominantly NBR. In certain embodiments it is substantially (90% or more by weight) NBR.

In at least one embodiment of the invention, the polymeric glove may be formed of latex having commonly used stabilizers such as potassium hydroxide, ammonia, sulfonates, and the like, which may be incorporated within any composition described herein. And, in at least one embodiment, the latex may contain other commonly used ingredients such as surfactants, anti-microbial agents, fillers/additives and the like. For NBR formulations, acrylonitrile content can in certain embodiments be, for example, about 28-about 34%, about 35-about 37%, or about 38-about 42%.

A fluid repellent coating, for example, a polymeric glove (or polymeric coating on a fabric liner of a supported glove) comprising a barrier coating, can be between about 2-20 mil (single-walled thickness) that provides protection against liquid permeability. Such gloves comprise, for example, NBR, NR, PI, CR, and PU, as discussed above, and further comprise a flow modifier (e.g., styrene-mono secondary butyl maleate-monomethyl maleate-maleic anhydride polymer), curative agents, germicide, pigments, and water.

Embodiments according to the invention include the use of a dispersion that comprises microparticles, for example, silica particles functionalized with fluorine chemistry, for example, HeiQ® Barrier RCF, and a fluorocarbon to promote the uniform dispersion of the microparticles, such as HeiQ® Barrier HM (both obtained from HeiQ® Materials AG). HeiQ® Barrier HM is a liquid formulation containing fluorine resin chemistry and auxiliary components to promote uniform coverage on the treatment surface. HeiQ® Barrier RCF is a liquid formulation containing specially engineered silicon dioxide (silica) particles that are functionalized with fluorine chemistry in amounts effective to increase fluid repellency on the exterior surface relative to the same barrier having only the hydrophobic chemical (in similar amounts). After forming the barrier article (after forming an elastomeric glove or coated fabric glove, by, for example, a dipping process) or, alternatively, using a preformed barrier article, the article is dipped into a formulation (for example, an aqueous formulation) of the hydrophobic micro-particles and/or the hydrophobic chemical. For example, a useful combination of hydrophobic micro-particles and hydrophobic chemical is HeiQ® Barrier RCF (for example at 10-100 g/L), and HeiQ® Barrier HM (for example at 20-110 g/L). If separate formulations are used, the hydrophobic chemical formulation can usefully be dipped second. Also, because the formulations are suspensions, stirring during dipping can be helpful.

The hydrophobic silica particles, as outlined above for the leak resistant surface, can also be used as the surface treatment opposing the hydrophilic glove surface.

The inner and outer gloves can be spot joined, such as by adhesive, heat fusion, spot welding, or the like. Adhesive joining can be with a heat-activated adhesive that is spot applied to one of the gloves, and activated when the gloves are layered, such as by IR lamp.

The exterior environment is a likely source of contamination, making it important to detect breaches in outer layers of a glove system. However, interior breaches also make the surgical worker (or the like) more vulnerable. As the surgical worker has worn the glove system for a period of time, some sweat builds, and provides the hydrophilic or aqueous fluid that creates the detectable contrast. Tests have shown that damp hand, analogous to hands with a small amount of sweat, are sufficient to create the warning contrast when there is a pin-hole in an inner glove.

Process of Forming Hydrophilic Surface

The process of forming the hydrophilic surface can include:

TABLE C

Applying a solution containing from about 0.05% to about 2% wt alkyl-aryl compound having a pendent from aryl one to two oxy-polymers, and optionally from about 0.01% to about 1% wt (a) a poly-oxyalkylene polymer that is predominantly oxyethylene or (b) a polyvinyl alcohol; and Drying the glove surface.

C. Tests

Various tests were performed on several gloves, including polyisoprene, natural rubber, and polychloroprene, according to embodiments of the invention as well as non-treated gloves for controls. Visual indicia of the efficacy of treatments according to the invention are shown and are labeled Experimental or Treated while prior art gloves are labeled Conventional or Control.

Visual repellency test with water: Glove according to embodiments of the invention and control gloves were mounted onto a former and immersed into an aqueous solution containing water and red pigment (Farsperse Red PR1123). Immediately after the withdrawal of each sample, the effect of water repellency on the glove surface was photographed.

Visual repellency test with human blood: Expired human blood sample (Type O, 2 months expired) collected from National Blood Bank, Kuala Lumpur, Malaysia was used for the test. Treated and control gloves were mounted onto a handed former and immersed in human blood at approximately 20° C. and withdrawn. Immediately following withdrawal, the glove surface was photographed showing the effect of blood repellency on the glove surface. The glove surface was then photographed again after 5 minutes.

Contact angle test: The liquid spread-ability of the glove surface was determined by a contact angle meter (AST Optima XE Video Contact Angle System, AST Products Inc.) by dropping a drop of water (7 microliters) and measuring the contact angle of the liquid on the elastomer surface immediately and after one or more further time periods, such as 5 seconds, 5 min., 10 min., 15 min., 20 min., 30 min. or 60 min. The measurement conditions were temperature 23±2° C.; relative humidity 55%+10%.

Tensile properties test: Tensile properties of control and treated gloves were tested according to ASTM D412. Tensometer Monsanto T10 was used to conduct the tensile test and dumbbell die cutter C was used. The accelerated aging of test specimens was carried out in accordance with ASTM D537-04. Irradiation created by Cobalt-60 Gamma ray source minimum dose of 2.5 mrads was used to sterilize the glove samples.

EXAMPLE 1

Breach Enhanced Detection gloves (as described in Ser. No. 14/806,132, filed 22 Jul. 2015, the glove having a hydrophilic outer surface) were used as undergloves and Control gloves or hydrophobic silica particle-coated gloves were used as the outer glove as specified. The outer glove was cut with a scissors to create a 3 mm cut linear hole on the index finger before donning over the under glove on a glove former. They were then dipped in water containing blue pigment in the same depth, where the center of the hole submersed to a depth of 30 mm, for 1 minute and 5 minutes. In another test, the glove system was dipped in expired human blood for 30 seconds and 5 minutes.

Figure 2B:
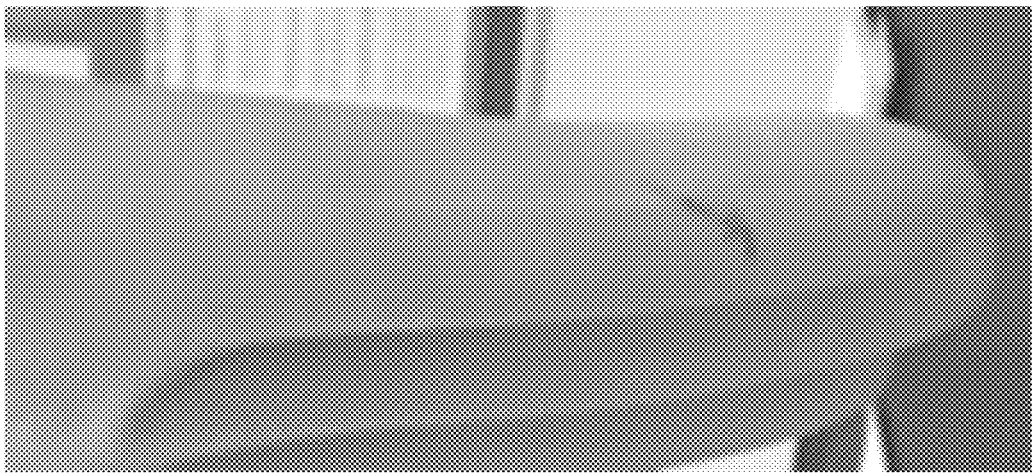
FIG. 2B shows the glove combination after 5 minute of dipping.

FIG. 1A shows a control outer glove (Ansell Textured Polyisoprene) in combination with the inner glove prior to dipping. The arrow shows the hole. FIG. 2B shows the glove combination after 1 minute of dipping. Liquid has moved by capillary action well up the finger in the space between the two gloves.

Figure 2A:
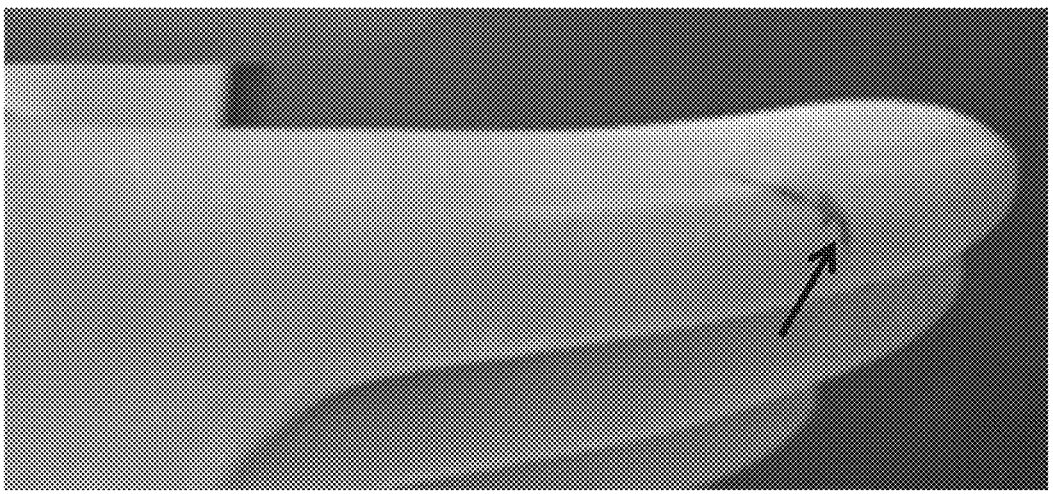
FIG. 2A shows an outer glove in combination with the inner glove after dipping in water for 1 minute.

FIG. 2A shows a hydrophobic silica particle-coated outer glove (Ansell Textured Polyisoprene) in combination with the inner glove after dipping in water for 1 minute. The arrow shows the hole. FIG. 2B shows the glove combination after 5 minute of dipping. Liquid migration is not seen at either time point.

Figure 3A:
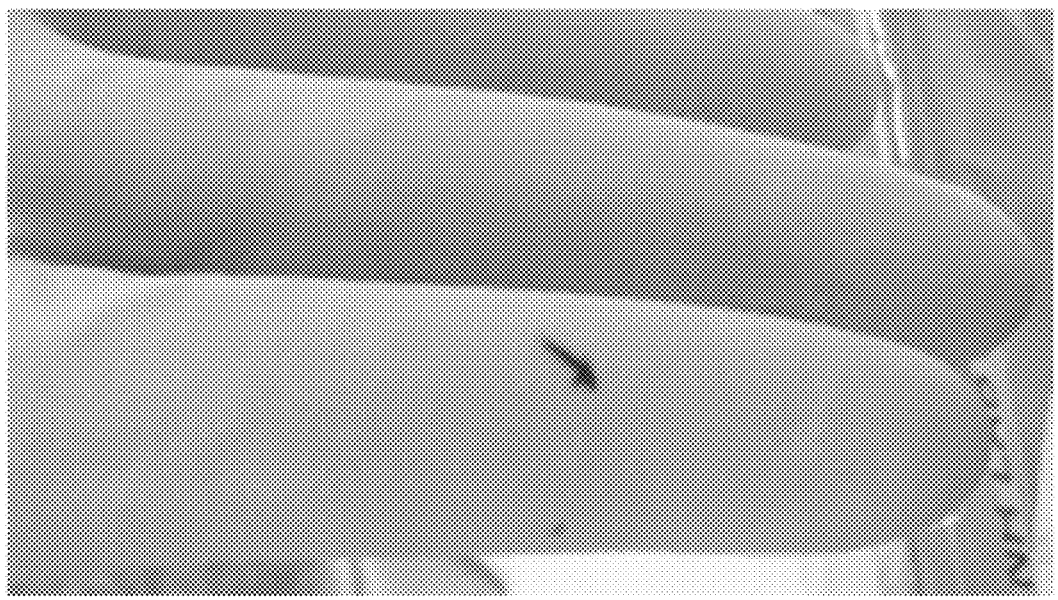
FIG. 3A shows an outer glove with a hydrophobic outer coating of the invention in combination with the inner glove after dipping in expired blood for 1 minute.
Figure 3B:
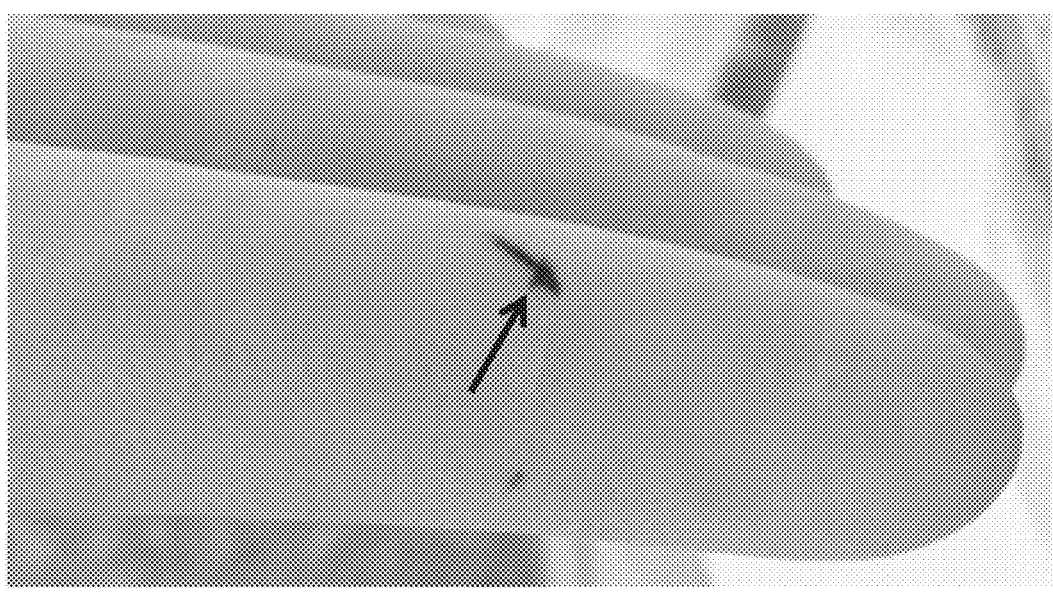
FIG. 3B shows the glove combination after 5 minute of dipping.

FIG. 3A shows a hydrophobic silica particle-coated outer glove (Ansell Textured Polyisoprene) in combination with the inner glove after dipping in expired blood for 1 minute. The arrow shows the hole. FIG. 3B shows the glove combination after 5 minute of dipping. Liquid migration is not seen at either time point.

EXAMPLE 2

PI gloves were treated to render them leak resistant according to the invention, and the water contact angle was measured initially, and over time. The results were:

| | Time interval (minute) | | | | | | |
|---|---|---|---|---|---|---|---|
| Glove side | 0 | 5 | 10 | 15 | 20 | 40 | 60 |
| Palm | 153 | 153 | 150 | 146 | 148 | 148 | 149 |
| Palm back | 152 | 146 | 154 | 147 | 156 | 147 | 157 |

EXAMPLE 3

Objectives:
1. To study the bacterial repellence efficacies of leak resistant outer gloves and breach detection (hydrophilic outer surface) under gloves against bacteria with human blood as the organic challenge.
2. To study the hydrophobicity property of the Hi-Viz gloves in contributing to the reduction in bacterial contamination on the Breach Detection gloves.

Figure 4A:
FIG. 4A shows a glove in preparation for bacterial resistance testing.
Figure 4B:
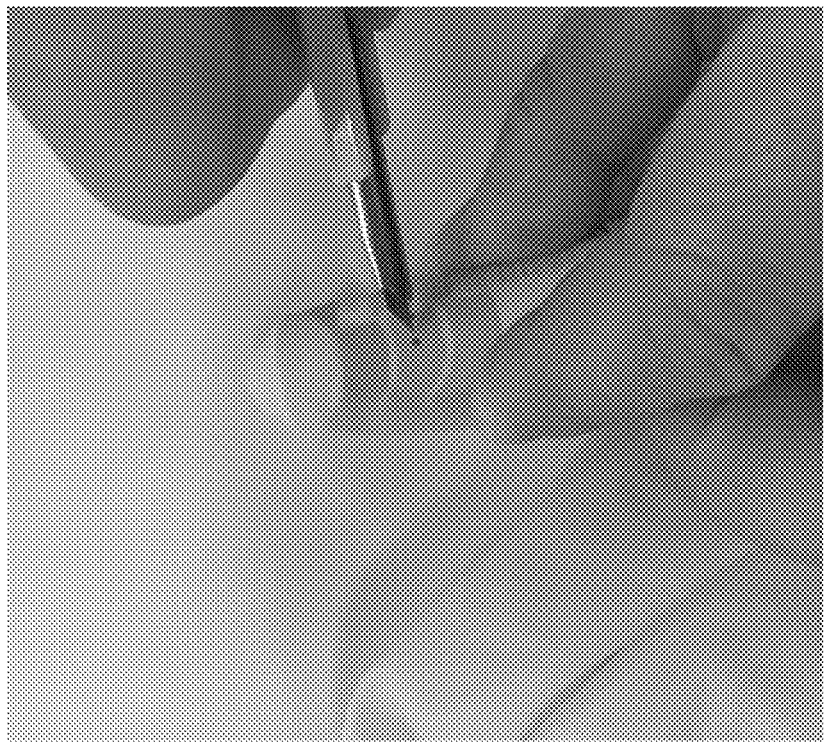
FIG. 4B shows the bacterial resistance test glove in further preparation for the testing.

Preparation of Glove Samples:
1. Use a caliper to measure and draw a line at 60 mm from finger-tip on the pointer finger of the sample and control outer gloves so that the desired area of exposure is achieved. At a distance of 30 mm from this line, draw two dots with a distance of 3 mm (FIG. 4A).
2. Carefully cut a hole between the two dots with a sharp knife (FIG. 4B).
3. Gamma radiate all the glove samples so that the gloves used in the study are sterile and bacteria of interest can be studied accurately.

Bacterial Species

A representative of Gram negative *E. coli* is used for this study.

Test Procedure

1. Conduct the test under Biological Safety Cabinet to prevent microbial contamination.
2. Don the under glove (breach detection PI glove) onto a first former followed by the outer glove (leak resistant glove with hole). This shall be the test sample.
3. Don the under glove (breach detection glove) onto a second former followed by the outer glove (standard PI glove, corresponding to breach detection glove save lacking the hydrophobic coating). This shall be the control sample.
4. Spike a human blood suspension with bacterial cells so that the final concentration of challenge bacterial suspended in human blood is at 10^6 CFU/mL.
5. For both samples, dip the glove finger donned on a former into the contaminated blood to the level that had been pre-marked for 5 minutes. Then lift up the former and allow to drip until the blood stops dripping. Photos are taken right after former is lifted up and after the dripping completed to visualize the physical repellence of the Hi-Viz glove to blood.
6. Remove the "dirty" portion of the outer glove by cutting above the dipped glove portion carefully without stretching the glove hole. Immerse the cut outer glove into 100 mL sterile saline and shake using orbital shaker for 1 minute for bacterial recovery.
7. Remove the dipped portion of the under glove by cutting the glove above the dipped glove portion. Immerse the cut under glove into 100 mL sterile saline and shake using orbital shaker for 1 minute for bacteria recovery.
8. Perform dilutions and plate counts from the glove samples suspended in 100 mL saline solutions.
9. Incubate the plates for 24-72 hours at 37 deg C.
10. Perform plate counts and calculate the bacterial recovery from the test and control gloves.

Results

The bacterial count results were as follows:

| Type of Glove | | Bacterial Recovery | | | |
|---|---|---|---|---|---|
| | | CFU/mL | CFU/sample | (Log10/mL) | CFU/cm$^2$ |
| Control glove | Outer gloves | 3.70E+04 | 2.96E+06 | 4.57 | 8.34E+04 |
| Leak resistant glove | | 1.14E+04 | 9.12E+05 | 4.06 | 2.57E+04 |
| Breach detection (Donned with control glove) | Under gloves | 1.00E+02 | 8.00E+03 | 2.00 | 2.25E+02 |
| Breach detection (Donned with leak resistant glove) | | <1.00 | <8.00E+01 | 0.00 | <2.25E+00 |

In this experiment, the bacteria act as a high sensitivity marker for leakage. Accordingly, the leak resistant glove was so successful in preventing a leak that the bacterial counts for the glove under the leak were essentially zero. The count with a standard glove used as the outer glove was at least two orders of magnitude higher.

Figure 5B:
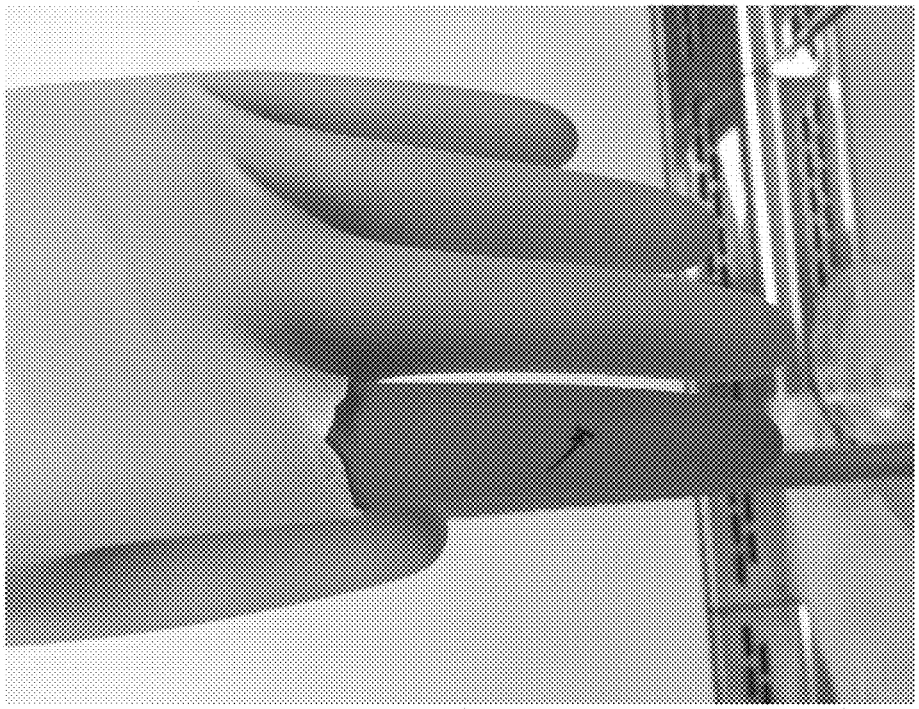
FIG. 5B shows leakage (or lack of leakage) to the inner glove from a leak resistant outer glove with a hole.
Figure 5A:
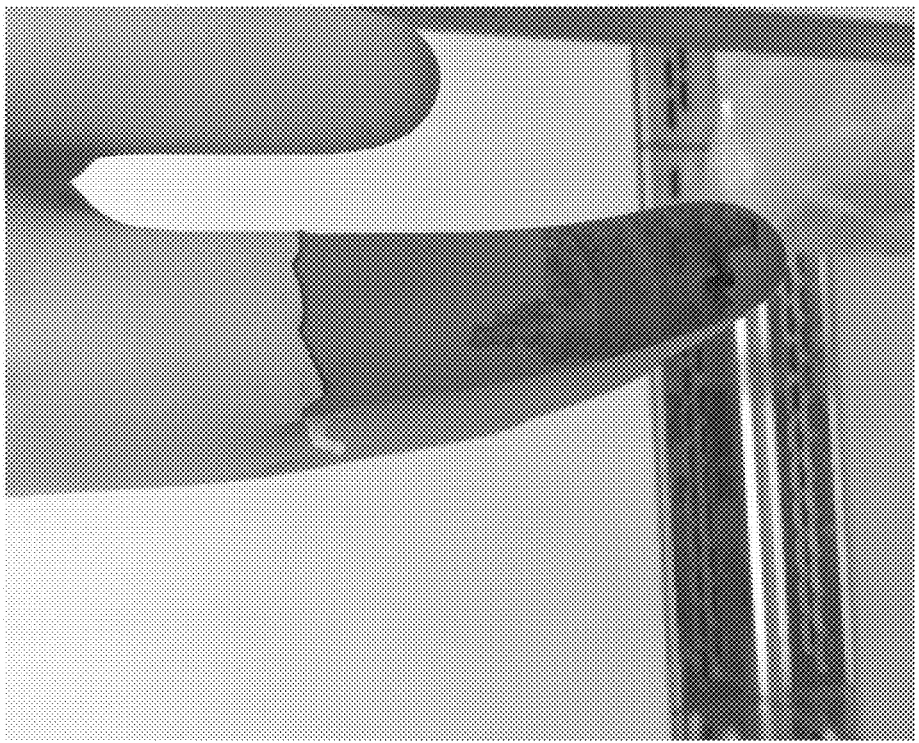
FIG. 5A shows leakage to the inner glove from a standard outer glove with a hole.

As outlined in the protocol above, the gloves are photographed after the outer glove material has been cut away. FIG. 5A shows the photograph where the control outer glove has been cut away. One can see extensive blood staining. FIG. 5B shows the photograph where the leak resistant outer glove has been cut away. No blood staining is apparent.

All ranges recited herein include ranges therebetween, inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4 . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent ranges starting at integer values at the recited order of magnitude or one lower, e.g., 3 or more includes 4 or more, or 3.1 or more. If there are two ranges mentioned, such as about 1 to 10 and about 2 to 5, those of skill will recognize that the implied ranges, for example of 1 to 5 and 2 to 10, are within the invention.

The invention can be further described with reference to the following numbered embodiments:

Embodiment 1: A leak-resistant elastomeric barrier comprising: an elastomeric barrier comprising elastomeric polymer, having two sides, and coated on at least a portion of a first side with highly hydrophobic coating such that the initial contact angle with water at 23+2° C. is about 130° or more, and that contact angle does not decay by more than about 10% over 40 minutes.

Embodiment 2: The leak-resistant elastomeric barrier of Embodiment 1, wherein the hydrophobic coating comprises hydrophobic silica particles.

Embodiment 3: The leak-resistant elastomeric barrier of one of Embodiments 1 and 2, wherein that contact angle does not decay by more than about 6% over 40 minutes.

Embodiment 4: The leak-resistant elastomeric barrier of one of Embodiments 2 and 3, wherein the hydrophobic silica particles are disposed on a hydrophobic coating disposed on the first side.

Embodiment 5: The leak-resistant elastomeric barrier of Embodiment 5, wherein the hydrophobic coating comprises a fluorocarbon compound, a polypropylene wax, a polyethylene wax, or a mixture thereof.

Embodiment 6: The leak-resistant elastomeric barrier of one of the numbered, wherein the barrier is formed to provide the hand protective part of a barrier glove.

Embodiment 7: The leak-resistant elastomeric barrier of Embodiment 6, wherein the barrier glove is a top, outer glove of a combination glove comprising a bottom, inner glove.

Embodiment 8: The combination glove of Embodiment 7, wherein the combination glove is for detecting breaches of hydrophilic or aqueous fluid wherein: (a) the top, barrier glove has an inner surface, namely the inner-barrier surface, the elastomer barrier of the top glove being translucent or transparent; (b) the bottom, backstop glove has an outer surface, namely the outer-backstop surface, the bottom glove comprising an elastomer layer that is darker than the top elastomer layer; and (c) there is a space or seam between the gloves in which the hydrophilic or aqueous fluid can flow, wherein to either the inner-barrier or the outer-backstop surface has been applied a hydrophilicity promoting composition, wherein the hydrophilicity promoting composition enhances the spreading in the space or seam of any of the hydrophilic or aqueous fluid that breaches the top elastomer or bottom layer.

Embodiment 9: The combination glove of Embodiment 8, wherein one of the inner-barrier or the outer-backstop surface has said hydrophilicity promoting composition, and the other is treated to render it hydrophobic.

Embodiment 10: The leak-resistant elastomeric barrier of one of the numbered Embodiments, wherein the leak-resistant elastomeric barrier resists leaking when a 3 mm linear cut hole therein is submerged in water for 1 minute at a depth of 30 mm.

Embodiment 11: The leak-resistant elastomeric barrier of one of the numbered Embodiments, wherein the leak-resistant elastomeric barrier resists leaking when a 3 mm linear cut hole therein is submerged in water for 5 minutes at a depth of 30 mm.

Embodiment 12: The leak-resistant elastomeric barrier of one of one of the numbered Embodiments, wherein the leak-resistant elastomeric barrier resists leaking when a 3 mm linear cut hole therein is submerged in blood for 30 seconds at a depth of 30 mm.

Embodiment 13: The leak-resistant elastomeric barrier of one of one of the numbered Embodiments, wherein the leak-resistant elastomeric barrier resists leaking when a 3 mm linear cut hole therein is submerged in blood for 5 minutes at a depth of 30 mm.

Embodiment 14: The leak-resistant elastomeric barrier of one of one of the numbered Embodiments, wherein the leak-resistant elastomeric barrier resists permeation of bacteria when a 3 mm linear cut hole therein is submerged in blood that is spiked with bacteria, with the submersion for 5 minutes at a depth of 30 mm.

Embodiment 15: A method of conducting surgery comprising: a surgical worker donning a glove or combination glove of one of one of the numbered Embodiments; and conducting a medical procedure in which the combination glove is exposed to biological fluids from a patient.

Embodiment 16: The method of Embodiment 15, further comprising replacing the combination glove when a leak is detected.

Embodiment 17: A method of forming the leak-resistant elastomeric barrier, comprising: applying a hydrophobic particle suspension to the elastomer surface (e.g., of one of the numbered Embodiments).

Embodiment 18: The method of forming of Embodiment 17, further comprising: prior to the hydrophobic particle application, applying a hydrophobic coating.

Embodiment 19: The method of forming of Embodiment 18, wherein applying the hydrophobic coating comprises applying a tie in layer comprising hydrophobic component and elastomer.

Embodiment 20: The method of Embodiment 19, wherein applying hydrophobic layer further comprises applying hydrophobic coating that is substantially free of elastomer.

Embodiment 21: The method of forming of one of Embodiments 17, 18 or 20, wherein applying the hydrophobic coating, or applying the hydrophobic particle suspension, or both, applying steps are by aerosol application.

Embodiment 22: The method of forming of one of Embodiments 17 to 20, comprising forming the elastomer surface on a former configured to impart structure on the elastomer surface that is effective to further limit wettability, over the surface with just the hydrophobic particle coating or just the hydrophobic coating and the hydrophobic particle coating, as the relevant comparative may be.

The foregoing description of embodiments of the invention comprises a elements, devices, machines, components and/or assemblies that perform various functions as described. These elements, devices, machines, components and/or assemblies are exemplary implementations of means for performing their functions.

Although only a few exemplary embodiments of the present invention have been described in detail above, those skilled in the art will readily appreciate that many modifications are possible in the exemplary embodiments without materially departing from the novel teachings and advantages of this invention.

What is claimed is:

1. A leak-resistant elastomeric barrier comprising:
an elastomeric barrier comprising elastomeric polymer, having two sides, and coated on at least a portion of a first side with highly hydrophobic coating such that the initial contact angle with water at 23±2° C. is about 130° or more, and that contact angle does not decay by more than about 10% over 40 minutes.

2. The leak-resistant elastomeric barrier of claim 1, wherein the hydrophobic coating comprises hydrophobic silica particles.

3. The leak-resistant elastomeric barrier of claim 1, wherein that contact angle does not decay by more than about 6% over 40 minutes.

4. The leak-resistant elastomeric barrier of claim 2, wherein the hydrophobic silica particles are disposed on a hydrophobic coating disposed on the first side.

5. The leak-resistant elastomeric barrier of claim 4, wherein the hydrophobic coating comprises a fluorocarbon compound, a polypropylene wax, a polyethylene wax, or a mixture thereof.

6. The leak-resistant elastomeric barrier of claim 1, wherein the barrier is formed to provide the hand protective part of a barrier glove.

7. The leak-resistant elastomeric barrier of claim 6, wherein the barrier glove is a top, outer glove of a combination glove comprising a bottom, inner glove.

8. The combination glove of claim 7, wherein the combination glove is for detecting breaches of hydrophilic or aqueous fluid wherein:
the top, barrier glove has an inner surface, namely the inner-barrier surface, the elastomer barrier of the top glove being translucent or transparent;
the bottom, backstop glove has an outer surface, namely the outer-backstop surface, the bottom glove comprising an elastomer layer that is darker than the top elastomer layer; and
there is a space or seam between the gloves in which the hydrophilic or aqueous fluid can flow,
wherein to either the inner-barrier or the outer-backstop surface has been applied a hydrophilicity promoting composition,
wherein the hydrophilicity promoting composition enhances the spreading in the space or seam of any of the hydrophilic or aqueous fluid that breaches the top elastomer or bottom layer.

9. The leak-resistant elastomeric barrier of claim 1, wherein the leak-resistant elastomeric barrier resists leaking when a 3 mm linear cut hole therein is submerged in water for 1 minute at a depth of 30 mm.

10. The leak-resistant elastomeric barrier of claim 1, wherein the leak-resistant elastomeric barrier resists leaking when a 3 mm linear cut hole therein is submerged in water for 5 minutes at a depth of 30 mm.

11. The leak-resistant elastomeric barrier of claim 1, wherein the leak-resistant elastomeric barrier resists leaking when a 3 mm linear cut hole therein is submerged in blood for 30 seconds at a depth of 30 mm.

12. The leak-resistant elastomeric barrier of claim 1, wherein the leak-resistant elastomeric barrier resists permeation of bacteria when a 3 mm linear cut hole therein is submerged in blood that is spiked with bacteria, with the submersion for 5 minutes at a depth of 30 mm.

13. A method of conducting surgery comprising:
   a surgical worker donning a combination glove of claim 7; and
   conducting a medical procedure in which the combination glove is exposed to biological fluids from a patient.

14. The method of claim 13, further comprising replacing the combination glove when a leak is detected.

15. A method of forming the leak-resistant elastomeric barrier of claim 1, comprising:
   applying a hydrophobic particle suspension to the elastomer surface.

16. The method of forming of claim 15, further comprising:
   prior to the hydrophobic particle application, applying a hydrophobic coating.

17. The method of forming of claim 16, wherein applying the hydrophobic coating comprises applying a tie in layer comprising hydrophobic component and elastomer.

18. The method of claim 17, wherein applying hydrophobic layer further comprises applying hydrophobic coating that is substantially free of elastomer.

19. The method of forming of claim 17, wherein applying the hydrophobic coating, or applying the hydrophobic particle suspension, or both, applying steps are by aerosol application.

20. The method of forming of claim 17, comprising forming the elastomer surface on a former configured to impart structure on the elastomer surface that is effective to further limit wettability, over the surface with just the hydrophobic particle coating or just the hydrophobic coating and the hydrophobic particle coating, as the relevant comparative may be.

21. The leak-resistant elastomeric barrier of claim 6, wherein the elastomeric polymer comprises polyisoprene.

22. The leak-resistant elastomeric barrier of claim 21, wherein the barrier has a textured surface structure on the first side of the elastomeric barrier that is effective to further limit wettability.

23. The leak-resistant elastomeric barrier of claim 6, wherein the elastomeric polymer is polyisoprene.

* * * * *